US006663888B2

(12) United States Patent
Percel et al.

(10) Patent No.: US 6,663,888 B2
(45) Date of Patent: Dec. 16, 2003

(54) PULSATILE RELEASE HISTAMINE H2 ANTAGONIST DOSAGE FORM

(75) Inventors: Philip J. Percel, Troy, OH (US); Nehal H. Vyas, Vandalia, OH (US); Krishna S. Vishnupad, Dayton, OH (US); Gopi M. Venkatesh, Dayton, OH (US)

(73) Assignee: Eurand Pharmaceuticals Ltd. (IE)

( * ) Notice: Subject to any disclaimer, the term of this patent is extended or adjusted under 35 U.S.C. 154(b) by 0 days.

(21) Appl. No.: 10/057,759

(22) Filed: Jan. 25, 2002

(65) Prior Publication Data

US 2003/0113374 A1 Jun. 19, 2003

Related U.S. Application Data

(60) Provisional application No. 60/340,419, filed on Dec. 14, 2001.

(51) Int. Cl.[7] .............................. A61K 9/52; A61K 9/54; A61K 9/60
(52) U.S. Cl. ...................... 424/457; 424/458; 424/459; 424/490; 514/965
(58) Field of Search .................... 424/459, 451, 424/457, 456, 462, 464, 490, 496, 497; 514/965

(56) References Cited

U.S. PATENT DOCUMENTS

| | | |
|---|---|---|
| 4,248,857 A | 2/1981 | DeNeale et al. |
| 4,728,512 A | 3/1988 | Mehta et al. |
| 4,851,229 A | 7/1989 | Magruder et al. |
| 4,863,742 A | 9/1989 | Panoz et al. |
| 4,871,549 A | 10/1989 | Ueda et al. |
| 4,894,240 A | 1/1990 | Geoghegan et al. |
| 4,915,949 A * | 4/1990 | Wong et al. ................. 424/438 |
| 4,983,401 A | 1/1991 | Eichel et al. |
| 5,011,692 A | 4/1991 | Fujioka et al. |
| 5,017,381 A | 5/1991 | Maruyama et al. |

(List continued on next page.)

FOREIGN PATENT DOCUMENTS

| | | |
|---|---|---|
| EP | 0239361 | 9/1987 |
| EP | 0391518 | 10/1990 |
| EP | 0431877 | 6/1991 |
| EP | 1010423 | 6/2000 |
| WO | 92/10173 | 6/1992 |
| WO | 00/25752 | 5/2000 |
| WO | 00/42998 | 7/2000 |
| WO | 01/13898 | 3/2001 |

Primary Examiner—Thurman K. Page
Assistant Examiner—Micah-Paul Young
(74) Attorney, Agent, or Firm—Thompson Hine LLP (57) ABSTRACT

A unit dosage form, such as a capsule or the like, for delivering drugs into the body in a circadian release fashion comprising one or more populations of drug-containing particles (beads, pellets, granules, etc.) is disclosed. Each bead population exhibits a pre-designed rapid or sustained release profile with or without a predetermined lag time of 3 to 5 hours. Such a circadian rhythm release drug delivery system is designed to provide a plasma concentration-time profile, which varies according to physiological need at different times during the dosing period, i.e., mimicking the circadian rhythm and severity/manifestation of gastric acid secretion (and/or midnight gerd), predicted based on pharmaco-kinetic and pharmaco-dynamic considerations and in vitro/in vivo correlations.

46 Claims, 5 Drawing Sheets

Circadian Variations in Gastric Acid Secretion

U.S. PATENT DOCUMENTS

| | | |
|---|---|---|
| 5,026,559 A | 6/1991 | Eichel et al. |
| 5,137,733 A | 8/1992 | Noda et al. |
| 5,213,808 A * | 5/1993 | Bar-Shalom et al. ....... 424/473 |
| 5,229,135 A | 7/1993 | Philippon et al. |
| 5,238,686 A | 8/1993 | Eichel et al. |
| 5,260,068 A | 11/1993 | Chen |
| 5,260,069 A | 11/1993 | Chen |
| 5,376,384 A | 12/1994 | Eichel et al. |
| 5,445,829 A | 8/1995 | Paradissis et al. |
| 5,470,584 A | 11/1995 | Hendrickson et al. |
| 5,478,573 A | 12/1995 | Eichel et al. |
| 5,508,040 A | 4/1996 | Chen |
| 5,529,790 A | 6/1996 | Eichel et al. |
| 5,536,507 A | 7/1996 | Abramowitz et al. |
| 5,567,441 A | 10/1996 | Chen |
| 5,616,345 A | 4/1997 | Geoghegan et al. |
| 5,629,017 A | 5/1997 | Pozzi et al. |
| 5,788,987 A | 8/1998 | Busettie et al. |
| 5,837,284 A | 11/1998 | Mehta et al. |
| 5,840,329 A | 11/1998 | Bai |
| 5,891,474 A | 4/1999 | Busetti et al. |
| 5,968,554 A | 10/1999 | Beiman et al. |
| 6,039,979 A | 3/2000 | Gendrot et al. |
| 6,162,463 A | 12/2000 | Lippa |
| 6,169,105 B1 | 1/2001 | Wong et al. |
| 6,190,692 B1 | 2/2001 | Busetti et al. |
| 6,228,398 B1 | 5/2001 | Devane et al. |
| 2001/0046964 A1 * | 11/2001 | Percel et al. |

* cited by examiner

Bioavailability of 150 mg Nizatidine CRR Vs 150 mg Nizatidine IR

PULSATILE RELEASE HISTAMINE H2 ANTAGONIST DOSAGE FORM

CROSS REFERENCES

This application claims the benefit of U.S. Provisional Application No. 60/340,419 filed Dec. 14, 2001.

TECHNICAL FIELD

A major objective of chronotherapy for indications such as asthma, gastric acid secretion and cardiovascular diseases is to deliver the drug in higher concentrations during the time of greatest need and in lesser concentrations when the need is less. Symptoms associated with "GERD" (Gastro Esophageal Reflux Disease) vary in severity throughout a 24-hour period. Accordingly, higher plasma concentrations of a histamine $H_2$ antagonist, such as nizatidine, are required to provide relief from acid secretion in response to fatty meals, as well as to attenuate the "midnight gerd" seen to occur in patients in response to the circadian rhythm to gastric acid secretion, while lower plasma concentrations are adequate in early morning hours and between meals. This is accomplished by administering a pulsatile release dosage form of the present invention, which provides a controlled release of an histamine $H_2$ antagonist from properly designed dosage forms. In particular, the present invention relates to a unit dosage form of an assembly of two or more bead populations, each of which is designed to release the therapeutic agent as a rapid or sustained release pulse after a predetermined delay with resulting plasma concentration varying in a circadian rhythm fashion, thereby enhancing patient compliance and therapeutic efficacy, reducing both cost of treatment and side effects.

BACKGROUND OF THE INVENTION

Many therapeutic agents are most effective when made available at a constant rate at or near the absorption site. The absorption of therapeutic agents thus made available generally result in desired plasma concentrations leading to maximum efficacy, minimum toxic side effects. Much effort has been devoted to developing sophisticated drug delivery systems, such as osmotic devices, for oral application. However, there are instances where maintaining a constant blood level of a drug is not desirable. For example, a "position-controlled" drug delivery system (e.g., treatment of colon disease or use of colon as an absorption site for peptide and protein based products) may prove to be more efficacious. A pulsatile delivery system is capable of providing one or more immediate release pulses at predetermined time points after a controlled lag time or at specific sites. However, there are only a few such orally applicable pulsatile release systems due to the potential limitation of the size or materials used for dosage forms. Ishino et al. disclose a dry-coated tablet form in Chemical Pharm. Bull. Vol. 40 (11), 3036–041 (1992). U.S. Pat. No. 4,851,229 to Magruder et al., U.S. Pat. No. 5,011,692 to Fujioka et al., U.S. Pat. No. 5,017,381 to Maruyama et al., U.S. Pat. No. 5,229,135 to Philippon et al., and U.S. Pat. No. 5,840,329 to Bai disclose preparation of pulsatile release systems. Some other devices are disclosed in U.S. Pat. No. 4,871,549 to Ueda et al. and U.S. Pat. Nos. 5,260,068; 5,260,069; and 5,508,040 to Chen. U.S. Pat. Nos. 5,229,135 and 5,567,441 both to Chen disclose a pulsatile release system consisting of pellets coated with delayed release or water insoluble polymeric membranes incorporating hydrophobic water insoluble agents or enteric polymers to alter membrane permeability. U.S. Pat. No. 5,837,284 to Mehta et al. discloses a dosage form which provides an immediate release dose of methylphenidate upon oral administration, followed by one or more additional doses spread over several hours.

Studies have shown that gastric acid secretion, especially the midnight gerd, follows a circadian rhythm. In such cases, administration of a different kind of unit dosage form which delivers the drug in higher concentrations during the time of greatest need, for example, around dinner and close to midnight, and in lesser concentrations at other times, is needed. Commonly assigned and co-pending U.S. application Ser. No. 09/778,645, which is incorporated in its entirety, discloses a pulsatile release system comprising a combination of two or three pellet populations, each with a well-defined release profile. In accordance with the present invention, a plasma profile is obtained which varies in a circadian rhythm fashion following administration of the novel dosage form.

SUMMARY OF THE INVENTION

The present invention provides a pulsatile release, multi-particulate dosage form comprising a mixture of two types of beads comprising a histamine $H_2$ receptor antagonist: IR (Immediate Release) Beads and TPR (Timed Pulsatile Release) Beads. Release profiles which approximate the daily fluctuations in gastric acid secretion are obtainable by blending IR Beads and TPR Beads at an appropriate ratio estimated from pharmaco-kinetic modeling. The IR Beads typically comprise two coatings applied to non-pareil seeds (# 25–30 mesh). The first coating contains a histamine $H_2$ antagonist and a binder, such as hydroxypropyl cellulose. The drug layered beads are coated with a seal coating of Opadry Clear to produce IR Beads. TPR Beads can be produced by applying a second functional membrane comprising a mixture of water insoluble polymer and an enteric polymer to IR Beads, both plasticized polymeric systems being applied from aqueous or solvent based systems.

The pulsatile release oral capsule formulation of the present invention comprises a combination of two types of spherical beads containing the active substance. IR (immediate release) Beads allow immediate release of the active while TPR Beads allow a delayed "burst" release (timed pulsatile release) of the active after a lag of 3–4 hours. When administered at bedtime (capsule containing IR Beads+TPR beads), the immediate release of the active is intended to provide relief from acid secretion in response to the meal, while the delayed "burst" is intended to attenuate the "midnight gerd" seen to occur in patients in response to the circadian rhythm to gastric acid secretion.

BRIEF DESCRIPTION OF THE DRAWINGS

The invention will be described in further detail with reference to the accompanying Figures wherein.

DETAILED DESCRIPTION OF THE INVENTION

The active core of the novel dosage form of the present invention may be comprised of an inert particle or an acidic or alkaline buffer crystal, which is coated with a drug-containing film-forming formulation and preferably a water-soluble film forming composition to form a water-soluble/dispersible particle. Alternatively, the active may be prepared by granulating and milling and/or by extrusion and spheronization of a polymer composition containing the drug substance. The amount of drug in the core will depend on the dose that is required, and typically varies from about 5 to 90 weight %. Generally, the polymeric coating on the active core will be from about 1 to 50% based on the weight of the coated particle, depending on the lag time and type of release profile required and/or the polymers and coating solvents chosen. Those skilled in the art will be able to select an appropriate amount of drug for coating onto or incorporating into the core to achieve the desired dosage. In one embodiment, the inactive core may be a sugar sphere or a buffer crystal or an encapsulated buffer crystal such as calcium carbonate, sodium bicarbonate, fumaric acid, tartaric acid, etc. which alters the microenvironment of the drug to facilitate its release.

To produce Timed Pulsatile Release (TPR) Beads, a water soluble/dispersible drug-containing particle is coated with a mixture of a water insoluble polymer and an enteric polymer, wherein the water insoluble polymer and the enteric polymer may be present at a weight ratio of from 4:1 to 1:1, and the total weight of the coatings is 10 to 60 weight % based on the total weight of the coated beads. The drug layered beads may optionally include an inner dissolution rate controlling membrane of ethylcellulose. The composition of the outer layer, as well as the individual weights of the inner and outer layers of the polymeric membrane are optimized for achieving desired circadian rhythm release profiles for a given active, which are predicted based on in vitro/in vivo correlations. In accordance with one embodiment of the present invention, a unit dosage form is provided wherein the unit dose comprises a mixture of immediate release beads (IR Beads, which are drug-containing particles without a dissolution rate controlling polymer membrane) and TPR Beads (drug containing particles with a coating of a blend of water insoluble polymer and enteric polymer exhibiting a lag time of 2–4 hours following oral administration), thus providing a two-pulse release profile. A unit dosage form, which does not comprise a rapid release bead population acting as a bolus dose, is also an embodiment of the present invention.

The present invention also provides a method of making a pulsatile release dosage form comprising a mixture of two bead populations comprising the steps of:

1. preparing a drug-containing core by coating an inert particle such as a non-pareil seed, an acidic buffer crystal or an alkaline buffer crystal with a drug and a polymeric binder or by granulation and milling or by extrusion/spheronization to form an immediate release (IR) bead;
2. coating the IR bead with a mixture of plasticized water-insoluble and enteric polymers to form a Timed Pulsatile Release (TPR) bead;
3. filling into hard gelatin capsules IR beads and TPR beads at a proper ratio to produce pulsatile capsules providing the desired release profile.

The release profile for TPR beads can be determined according to the following procedure:

Dissolution Procedure:

Dissolution Apparatus: USP Apparatus 2 (Paddles at 50 rpm) using a two-stage dissolution medium (first 2 hrs in 700 mL 0.1N HCl at 37° C. followed by dissolution at pH=6.8 obtained by the addition of 200 mL of pH modifier) and Drug Release determination by HPLC).

The TSR Beads prepared in accordance with present invention release, when tested by the above procedure, not more than 25%, more preferably not more than 15%, and most preferably not more than 5% in 2 hours, about 15–80%, more preferably about 20–65%, and most preferably about 30–50% in 3 hours, and not less than 60%, more preferably not less than 70%, and most preferably not less than 80% in 4 hrs.

Dosage forms in accordance with the present invention typically comprise a combination of IR Beads and TPR Beads at a ratio from 3:1 to 1:3, preferably a ratio from 2:1 to 1:2. In accordance with certain embodiments, the ratio of IR Beads to TPR Beads is approximately 1:1.

The histamine $H_2$ receptor antagonists suitable for incorporation into these circadian rhythm release (CRR) drug delivery systems include acidic, basic, zwitterion, or neutral bioactive molecules or their salts indicated for the treatment of active duodenal ulcer, such as nizatidine, cimetidine, ranitidine, and famotidine.

An aqueous or a pharmaceutically acceptable solvent medium may be used for preparing drug-containing core particles. The type of film forming binder that is used to bind the drug to the inert sugar sphere is not critical but usually water soluble, alcohol soluble or acetone/water soluble binders are used. Binders such as polyvinylpyrrolidone (PVP), polyethylene oxide, hydroxypropyl methylcellulose (HPMC), hydroxypropylcellulose (HPC), polysaccharides such as dextran, corn starch may be used at concentrations of 0.5 to 5 weight %. The drug substance may be present in this coating formulation in the solution form or may be dispersed at a solid content up to 35 weight % depending on the viscosity of the coating formulation.

The drug substance, a binder such as PVP, a dissolution rate controlling polymer (if used), and optionally other pharmaceutically acceptable excipients are blended together in a planetary mixer or a high shear granulator such as Fielder and granulated by adding/spraying a granulating fluid such as water or alcohol. The wet mass can be extruded and spheronized to produce spherical particles (beads) using an extruder/marumerizer. In these embodiments, the drug load could be as high as 90% by weight based on the total weight of the extruded/spheronized core.

The active containing cores (beads, pellets or granular particles) thus obtained may be coated with one or two layers of dissolution rate controlling polymers to obtain desired release profiles with or without a lag time. The inner layer membrane largely controls the rate of drug release following imbibition of water or body fluids into the core while the outer layer membrane provides for the desired lag time (the period of no or little drug release following imbibition of water or body fluids into the core). The inner layer membrane may comprise a water insoluble polymer, or a mixture of water insoluble and water soluble polymers.

Representative examples of water insoluble polymers useful in the invention include ethylcellulose, polyvinyl acetate (Kollicoat SR#0D from BASF), neutral copolymers based on ethyl acrylate and methylmethacrylate, copolymers of acrylic and methacrylic acid esters with quaternary ammonium groups such as Eudragit NE, RS and RS30D, RL or RL30D and the like. Representative examples of water soluble polymers are low molecular weight HPMC, HPC, methylcellulose, polyethylene glycol (PEG of molecular weight>3000) at a thickness ranging from 1 weight % up to 10 weight % depending on the solubility of the active in water and the solvent or latex suspension based coating formulation used. The water insoluble polymer to water soluble polymer may typically vary from 95:5 to 60:40, preferably from 80:20 to 65:35.

The polymers suitable for the outer membrane, which largely controls the lag time of up to 6 hours may comprise an enteric polymer and a water insoluble polymer at a thickness of 10 to 50 weight %. The ratio of water insoluble polymer to enteric polymer may vary from 4:1 to 1:2, preferably the polymers are present at a ratio of about 1:1. The water insoluble polymer typically used is ethylcellulose.

Representative examples of enteric polymers useful in the invention include esters of cellulose and its derivatives (cellulose acetate phthalate, hydroxypropyl methylcellulose phthalate, hydroxypropyl methylcellulose acetate succinate), polyvinyl acetate phthalate, pH-sensitive methacrylic acid-methacrylate copolymers and shellac. These polymers may be used as a dry powder or an aqueous dispersion. Some commercially available materials that may be used are methacrylic acid copolymers sold under the trademark Eudragit (L100, S100, L30D) manufactured by Rhom Pharma, Cellacefate (cellulose acetate phthalate) from Eastman Chemical Co., Aquateric (cellulose acetate phthalate aqueous dispersion) from FMC Corp. and Aqoat (hydroxypropyl methylcellulose acetate succinate aqueous dispersion) from Shin Etsu K. K.

Both enteric and water insoluble polymers used in forming the membranes are usually plasticized. Representative examples of plasticizers that may be used to plasticize the membranes include triacetin, tributyl citrate, triethyl citrate, acetyl tri-n-butyl citrate diethyl phthalate, castor oil, dibutyl sebacate, acetylated monoglycerides and the like or mixtures thereof. The plasticizer may comprise about 3 to 30 wt. % and more typically about 10 to 25 wt. % based on the polymer. The type of plasticizer and its content depends on the polymer or polymers, nature of the coating system (e.g., aqueous or solvent based, solution or dispersion based and the total solids).

In general, it is desirable to prime the surface of the particle before applying the pulsatile release membrane coatings or to separate the different membrane layers by applying a thin hydroxypropyl methylcellulose (HPMC) (Opadry Clear) film. While HPMC is typically used, other primers such as hydroxypropylcellulose (HPC) can also be used.

The membrane coatings can be applied to the core using any of the coating techniques commonly used in the pharmaceutical industry, but fluid bed coating is particularly useful.

The present invention is applied to multi-dose forms, i.e., drug products in the form of multi-particulate dosage forms (pellets, beads, granules or mini-tablets) or in other forms suitable for oral administration.

The following Examples illustrate the dosage formulations of the invention.

EXAMPLES

Pulsatile Release capsules of nizatidine, a novel histamine $H_2$ receptor antagonist, comprise a mixture of two sets of beads: The first set is referred to as immediate release (IR) Beads and are designed to provide a loading dose by releasing all of the nizatidine within the first hour, preferably within the first 30 minutes. The second set is referred to as the Timed Pulsatile Release (TPR) Beads and are designed to release nizatidine in a 'burst' over a period of 2 hours after about 2–4 hour lag time. The TPR Beads are produced by applying an outer layer of pulse coating (comprising a blend of an enteric polymer such as HPMCP and a water insoluble polymer such as ethylcellulose) on IR Beads. The two sets of beads when filled into capsule shells at an appropriate ratio will produce the target circadian rhythm release profile required for maintaining drug plasma concentrations at potentially beneficial level when taken orally twice a day, after breakfast and dinner.

Example 1

Figure 1:
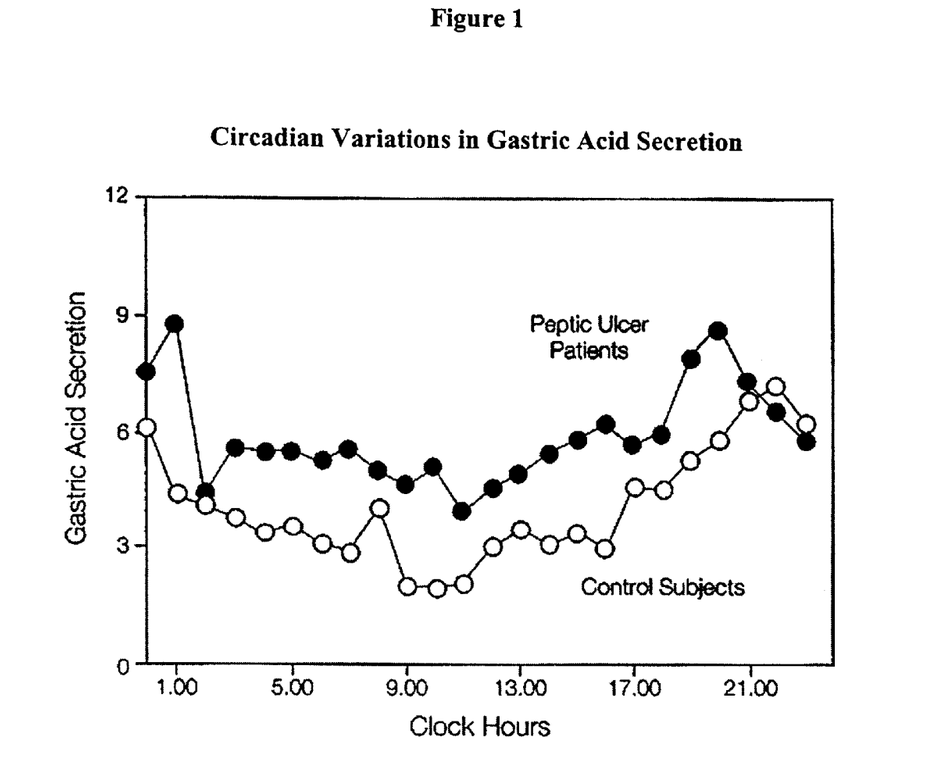
FIG. 1 shows Circadian Rhythm variations in gastric acid secretion (Reference: the presentation by Gordon L. Amidon at the Formulation Optimization and Clinical Pharmacology, a Capsugel Sponsored Conference at Tokyo, Apr. 23, 1999, p. 16).
Figure 2:
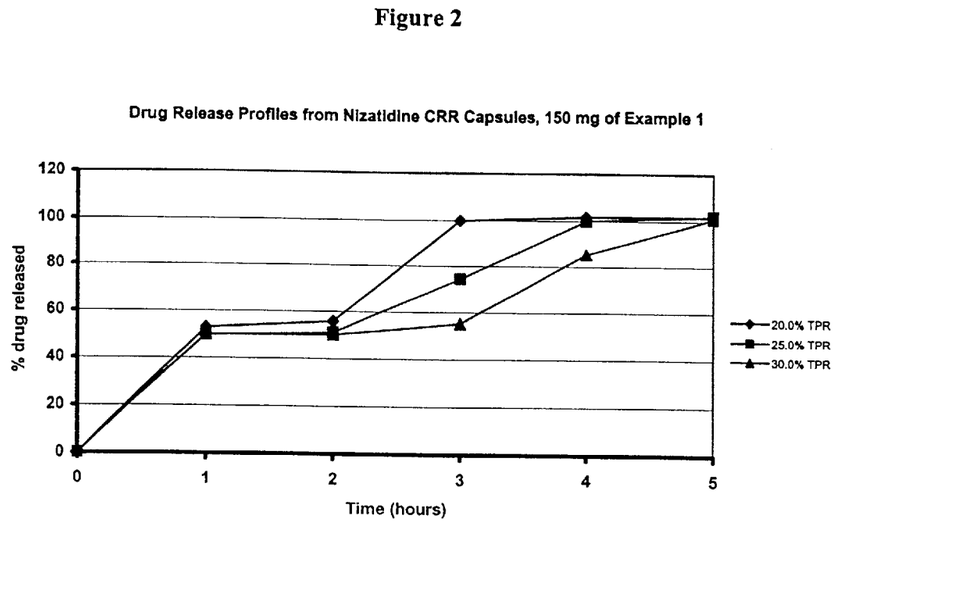
FIG. 2 shows the drug release profiles from Nizatidine Pulsatile Capsules, 150 mg (75 mg IR Beads+75 mg TPR Beads) of Example 1, wherein the TPR Beads have different pulse coating levels.

Nizatidine (5787.7 g) was slowly added to an aqueous solution of hydroxypropylcellulose such as Klucel LF (643.1 g) and mixed well. # 25–30 mesh sugar spheres (3700 g) were coated with the drug suspension in a Glatt fluid bed coater. The drug containing particles were dried, and a seal coat of Opadry Clear (2% w/w) was first applied. These drug containing IR Beads were provided with an outer membrane by spraying a solution of 1:1 blend of ethylcellulose and HPMCP plasticized with diethyl phthalate in 98/2 acetone/water in a fluid bed coater for a weight gain of approximately 39–40%. The coated particles are cured at 60° C. until the polymers were coalesced to produce TPR Beads. Pulsatile Release Nizatidine Capsules, 150 mg, were manufactured by filling 75 mg IR Beads and 75 mg TPR Beads into size 0 hard gelatin capsules using a MG Futura capsule filling equipment. The drug release testing was performed using USP Apparatus 2 (Paddles @ 50 rpm) in 0.1N HCl for 2 hours and subsequently at pH 6.8. The release profiles generated from Pulsatile Release Capsules comprising TPR Beads with different membrane coating levels are presented in FIG. 2.

Example 2

Figure 3:
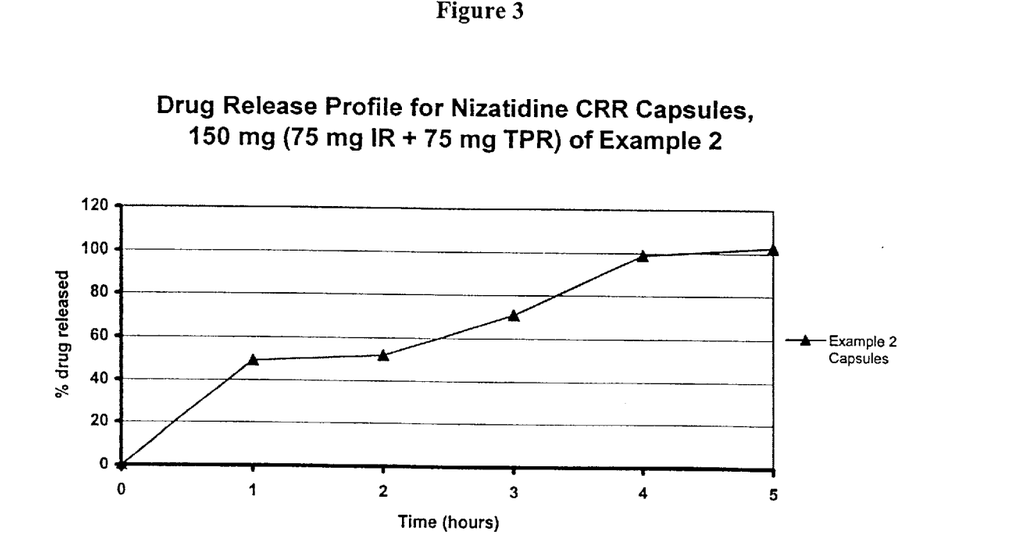
FIG. 3 shows the drug release profile for Nizatidine Pulsatile Capsules, 150 mg (75 mg IR Beads+75 mg TPR Beads) of Example 2.

Nizatidine (168 kg) was slowly added to an aqueous solution of hydroxypropylcellulose such as Klucel LF (18.6 kg) and mixed well. # 25–30 mesh sugar spheres (107.4 kg) were coated with the drug suspension in a Glatt fluid bed coater, equipped with a 32" bottom spray Wurster insert. The drug containing particles were dried, and a seal coat of Opadry Clear (2% w/w) was first applied and dried in the Glatt fluid bed unit as a precautionary measure to drive off excessive surface moisture. These drug containing IR Beads were provided with an outer membrane by spraying a solution of 1:1 blend of ethylcellulose and HPMCP plasticized with diethyl phthalate in 98/2 acetone/water in a fluid bed coater for a weight gain of approximately 39–40%. The coated particles are cured at 60° C. for 4 hours to produce TPR Beads (batch size: 300 kg). Pulsatile Release Nizatidine Capsules, 150 mg, were manufactured by filling 75 mg IR Beads and 75 mg TPR beads into size 0 hard gelatin capsules. The drug release profile is shown in FIG. 3.

Example 3

Figure 4:
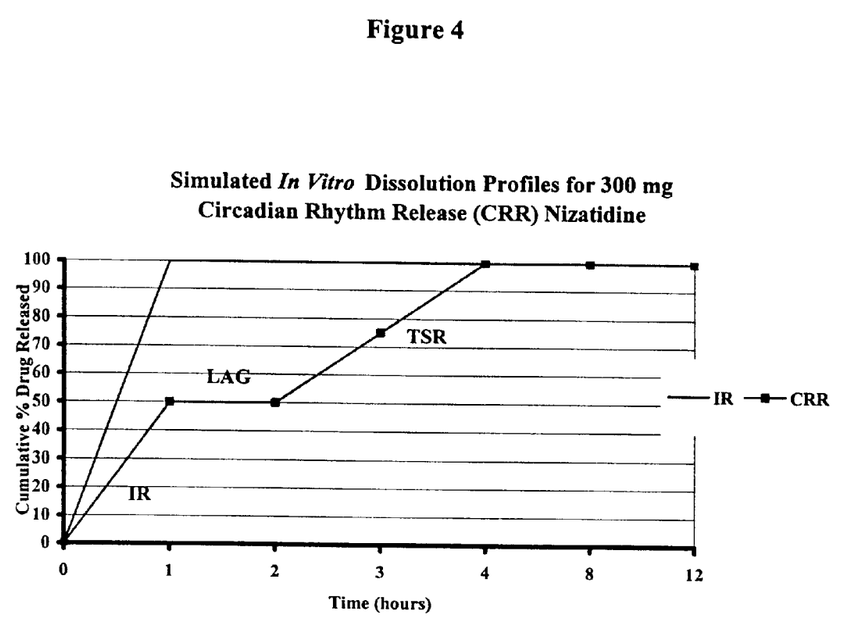
FIG. 4 shows the target or simulated in vitro drug release profile used in PK simulation.
Figure 5A:
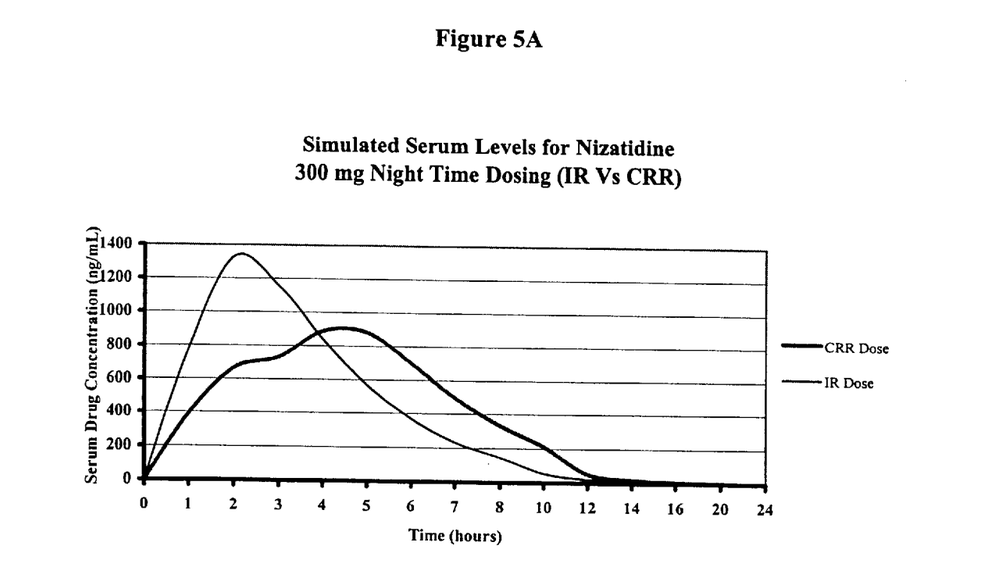
FIG. 5 compares the simulated plasma levels of Nizatidine Pulsatile Capsule versus 300 mg IR Dose following oral administration at (a) night time and (b) day time.
Figure 5B:
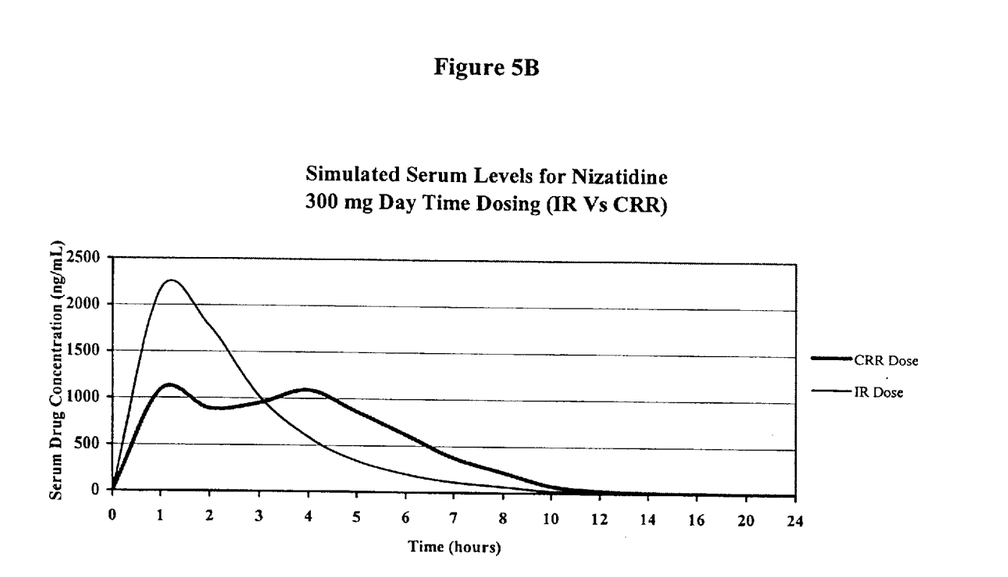

In order to assess the type of in vitro release profile needed to achieve a circadian rhythm effect under in vivo conditions, a modeling exercise was performed using the pharmacokinetic parameters for nizatidine. A diurnal variation in the pharmaco-kinetics of nizatidine has been reported by Jamali, A. Thomson, P. Kirdeikis, M. Tavernini, L. Zuk, R. Marriage, R. Simpson, and V. Mahachai (the reference entitled, "Diurnal variation in the pharmaco-kinetics of Nizatidine in healthy volunteers and in patients with peptic ulcer disease", *Journal of Clinical Pharmacology* 35:1071–1075, 1995 is incorporated in its entirety). A pharmaco-kinetic modeling was done separately to try to mimic both night time and day time results individually. Mean serum concentrations of nizatidine achieved in healthy volunteers were taken from the same literature. Theoretical in vitro dissolution profile (FIG. 4) as well as in vivo serum levels achieved during nighttime and daytime dosing, were simulated using the pharmaco-kinetic models developed. The advantages of a pulsatile dosage form are evident in attached FIG. 5 that compares simulated serum levels achieved with an immediate release dose of nizatidine versus the proposed pulsatile dose, being orally administered at (a) nighttime and (b) daytime. The proposed dosage form is seen to give two pulses about 3.5–4.0 hours apart, maintaining an acceptable serum concentration for about 6.0–8.0 hours in the body, irrespective of whether night time or day time dosing is considered. Thus, the presence of the TPR portion should ideally sustain enough drug in the body right around midnight when literature has reported a circadian rhythm to gastric acid secretion and increased severity of symptoms associated with GERD.

Figure 6:
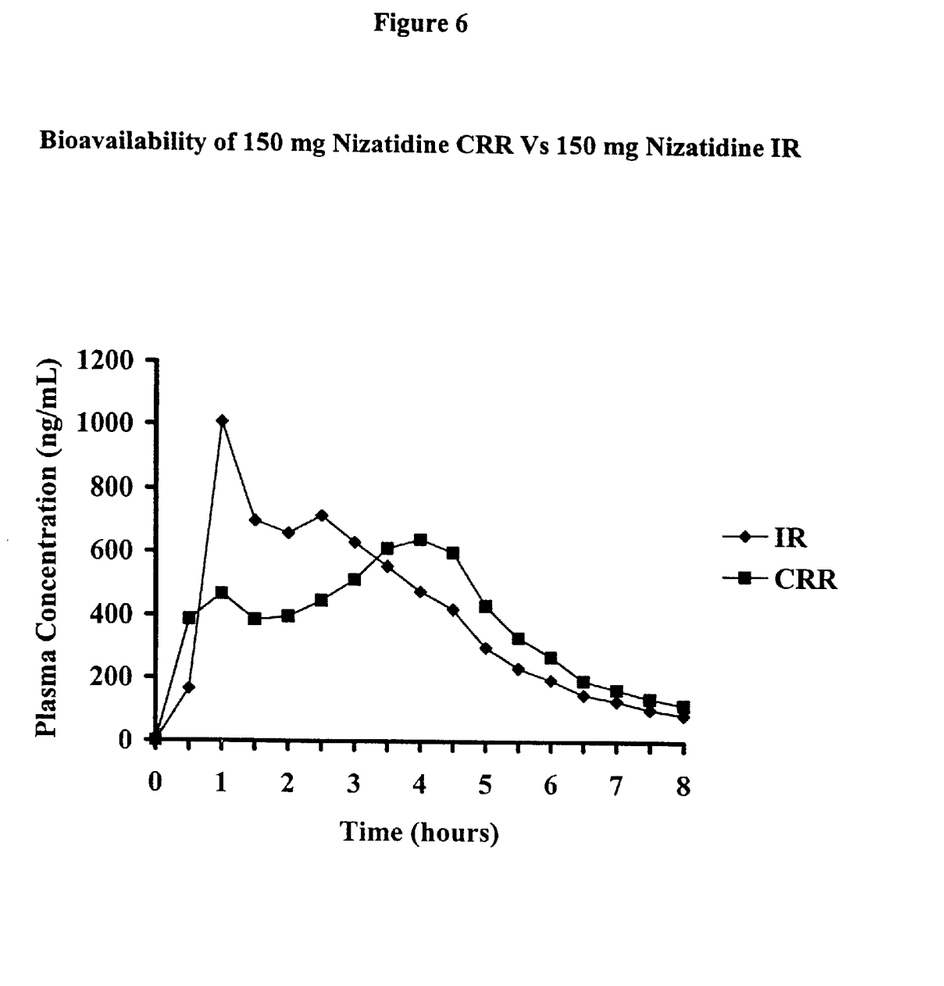
FIG. 6 shows the plasma level of Nizatidine following oral administration in a healthy volunteer when dosed after dinner with Pulsatile Capsule, 150 mg (75 mg IR Beads+75 mg TPR Beads) (a bimodal display) versus 150 mg IR Dose.

Clinical supplies, nizatidine pulsatile Capsules, 150 mg, comprising of 75 mg IR and 75 mg TPR Beads were manufactured following Example 1, by filling hard gelatin size# 0 capsules. FIG. 6 shows the plasma concentration profile (a bimodal display) achieved in a healthy volunteer when dosed after dinner.

Example 4

The nizatidine pulsatile Capsules prepared in Example 3 were utilized in two randomized, double-blind, comparative, multiple dose efficacy studies. The clinical efficacy studies included a total of 428 subjects with GERD who were treated with the subject nizatidine Capsules and 215 treated with placebo. For the purpose of summarizing the nizatidine Capsules efficacy data, the two randomized, double-blind, comparative, multiple dose efficacy studies were conducted under identical protocols during the same time period, and identical case report forms were used for both studies. Clinical studies were designed to assess the safety and efficacy of nizatidine Capsules 150 mg bid, nizatidine Capsules 300 mg and placebo in adult subjects with clinical symptom and endoscopic evidence of erosive and ulcerative GERD. Subjects meeting the entry criteria were randomized to receive one of the three treatments and began taking study medication in the evening on Day 0. Study medication was taken for up to 12 weeks, with follow-up visits at weeks 3,6 and 12.

The results of the combined efficacy analyses indicated that clinically and statistically significant healing of erosive esophagitis with associated symptom relief was produced by the nizatidine Capsules administered either as individual doses (150 mg bid) or as a single nightly dose of 300 mg. For the nizatidine Capsule 150 mg bid, statistically significant and clinically meaningful overall healing was also demonstrated. Subjects treated with nizatidine Capsules bid had a significantly greater mean change from baseline in their endoscopy grade and there was a notable trend toward efficacy in the proportions of subjects who had $\geq 2$ points improvement in baseline endoscopy grade compared to those treated with placebo. Subjects treated with nizatidine Capsules 300 mg qd also had a greater mean change from baseline in their endoscopy grade. Based on subject rated nighttime symptom scores, statistically significant and clinically meaningful night time relief of heartburn, regurgitation and retrosternal pain was demonstrated during the first week of treatment for both nizatidine Capsules 150 mg bid and nizatidine Capsules 300 mg qd. Based on Investigator-rated night time symptom scores, treatment with nizatine Capsules 150 mg bid was significantly superior to placebo at Week 12 for heartburn and regurgitation, and there a trend toward efficacy for retrosternal pain. Treatment with nizatidine Capsules 300 mg qd was significantly superior to placebo at Week 12 for heartburn, regurgitation and retrosternal pain. Based on Investigator rated daytime symptom scores, treatment with nizatidine Capsules 150 mg bid was significantly superior to placebo at Week 12 for daytime heartburn and retrosternal pain. Nizatidine Capsules 300 mg qd was significantly superior to placebo at Week 12 for daytime retrosternal pain. Subjects treated with nizatidine Capsules 150 mg bid used significantly less antacid tablets per day than did those treated with placebo (P<0.001).

The study conclusion was as follows:

"Overall, in subjects with endoscopically proven GERD, nizatidine CR administered in doses of either 150 mg bid or 300 mg qd was effective in healing esophageal erosions and in relieving GERD symptoms."

Example 5

Cimetidine was slowly added to an aqueous solution of polyvinylpyrrolidone and mixed well. # 25–30 mesh sugar spheres were coated with drug solution in a Glatt fluid bed granulator. The drug containing pellets were dried, and a seal coat of Opadry Clear (2% w/w) was first applied. The inner polymer coating was applied to the active particles by spraying an aqueous dispersion of ethylcellulose (aquacoat® ECD-30 with dibutyl sebacate as the plasticizer to produce intermediate release (IntR) Beads. An outer coating formulation was prepared by mixing two separate aqueous dispersions of Eudragit L30D plasticized with acetyl tri-n-butyl citrate and Aquacoat ECD-30 (an aqueous dispersion of ethylcellulose) plasticized with dibutyl sebacate. The combined coating formulation was sprayed onto the ethylcellulose coated IntR Beads. The coated particles are cured at 60° C. until the polymers were coalesced to produce TSR Beads. The finished SR and TSR Beads were tested for in vitro dissolution properties using USP Dissolution Apparatus 2 at a paddle speed of 50 rpm. The beads were dissoluted using a three-stage dissolution medium, i.e., first 2 hours in 0.1N HCl, next 2 hours at pH 4.0 and then at pH 6.8 for additional 14 hours, the pH of the medium being changed by adding a pH modifier. The results obtained are presented in Table 1. The dissolution results show that there is a lag time of about four hours followed by sustained release occurring over a period of 12–14 hours for the TSR Beads.

TABLE 1

Dissolution Data for SR and TSR Beads of Example 4

| Time, hours | SR Beads SR Coating (1.8% w/w) | TSR Beads SR Coating (1.8% w/w) / TSR Coating (15% w/w) |
|---|---|---|
| 1.0 | 0.2 | 0 |
| 2.0 | 0.1 | 0 |
| 3.0 | 0.5 | 0.5 |
| 4.0 | 0.2 | 0.4 |
| 5.0 | 15 | 10 |

TABLE 1-continued

Dissolution Data for SR and TSR Beads of Example 4

| Time, hours | SR Beads SR Coating (1.8% w/w) | TSR Beads SR Coating (1.8% w/w) / TSR Coating (15% w/w) |
|---|---|---|
| 6.0 | 42 | 24 |
| 8.0 | 71 | 47 |
| 10.0 | 85 | 62 |
| 12.0 | 93 | 72 |
| 14.0 | 98 | 78 |
| 16.0 | 103 | 86 |

We claim:

1. A histamine $H_2$ antagonist pharmaceutical dosage form providing a bi-modal pulsatile release profile comprising:
    a. immediate release (IR) beads comprising an active-containing core particle; and
    b. timed pulsatile release (TPR) beads, wherein said TPR beads comprise:
        i. an active-containing core particle; and
        ii. a pulse coating comprising a water insoluble polymer and an enteric polymer surrounding said core,
    said timed pulsatile release (TPR) beads when tested in a USP Type II apparatus at 50 rpm using a 2-stage dissolution medium (first 2 hours in 700 ml 0.1 N HCl at 37° C. followed by a dissolution in a pH of 6.8 obtained by the addition of 200 ml of pH modifier) exhibit a dissolution profile substantially corresponding to the following pattern:
        after 2 hours, 0–25% of the total active is released;
        after 3 hours, 15–80% of the total active is released; and
        after 4 hours, not less than 60% of the total active is released,
        wherein said IR beads provide a therapeutically effective amount of active to treat gastric acid secretions and the TPR beads provide a delayed dose of active which provides a therapeutically effective amount of active to treat midnight GERD.

2. A pharmaceutical dosage form as defined in claim 1, wherein said histamine $H_2$ receptor antagonist is selected from the group consisting of nizatidine, cimetidine, ranitidine, and famotidine and derivatives thereof.

3. A pharmaceutical dosage form as defined in claim 1, wherein said dissolution profile substantially corresponds to the following pattern:
    after 2 hours, 0–15% of the total active is released;
    after 3 hours, 20–65% of the total active is released; and
    after 4 hours, not less than 70% of the total active is released.

4. A pharmaceutical dosage form as defined in claim 3, wherein said dissolution profile substantially corresponds to the following pattern:
    after 2 hours, 0–5% of the total active is released;
    after 3 hours, 30–50% of the total active is released; and
    after 4 hours, not less than 80% of the total active is released.

5. A pharmaceutical dosage form as defined in claim 1, wherein said enteric polymer is selected from the group consisting of esters of cellulose, polyvinyl acetate phthalate, pH-sensitive methacrylic acid-methylmethacrylate copolymers, shellac and derivatives thereof.

6. A pharmaceutical dosage form as defined in claim 5, wherein said enteric polymer is selected from the group consisting of cellulose acetate phthalate, hydroxypropyl methylcellulose phthalate, hydroxypropyl methylcellulose succinate and combinations thereof.

7. A pharmaceutical dosage form as defined in claim 5, wherein at least one of said polymers further comprises a plasticizer.

8. A pharmaceutical dosage form as defined in claim 7, wherein said plasticizer is selected from the group of triacetin, tributyl citrate, tri-ethyl citrate, acetyl tri-n-butyl citrate, diethyl phthalate, dibutyl sebacate, polyethylene glycol, polypropylene glycol, castor oil and acetylated mono- and di-glycerides and mixtures thereof.

9. A dosage form as defined in claim 1, wherein said water insoluble polymer and said enteric polymer are present in said pulse release coating at a ratio from 4:1 to 1:2.

10. A dosage form as defined in claim 9, wherein said ratio of water insoluble polymer to enteric polymer is from 2:1 to 1:1.

11. A dosage form as defined in claim 9, wherein said water insoluble polymer is ethylcellulose and said enteric polymer is hydroxypropyl methylcellulose phthalate.

12. A dosage form as defined in claim 11, wherein said ratio is approximately 1:1.

13. A dosage form as defined in claim 1, wherein said IR beads provide a loading dose by releasing substantially all of the active contained in said IR beads within the first hour after administration of the dosage form.

14. A dosage form as defined in claim 1, wherein said IR beads and TPR beads are present in a ratio from about 3:1 to 1:3.

15. A dosage form as defined in claim 14, wherein said IR beads and TPR beads are present in a ratio from about 2:1 to 1:2.

16. A dosage form as defined in claim 1, wherein the total weight of the coatings on the TPR beads is 10–60 weight % based on the total weight of the coated particles.

17. A method for the preparation of the dosage form of claim 1, comprising the steps of:
    a. preparing an active-containing core to form IR beads;
    b. coating the IR bead with a mixture of plasticized water soluble polymer and an enteric polymer to form a TPR bead; and
    c. filling capsules with IR beads and TPR beads at a ratio from 3:1 to 1:3.

18. The method of claim 17, wherein said active-containing core is produced by coating a particle selected from the group consisting of non-pareil seeds, acidic buffer crystals and alkaline buffer crystals with a water soluble film-forming composition comprising nizatidine and a polymeric binder.

19. The method of claim 17, wherein said active-containing core is produced by granulating and milling and/or by extrusion and spheronization of a polymer composition containing nizatidine.

20. A pulsatile release nizatidine dosage form comprising:
    a. immediate release (IR) beads comprising a nizatidine-containing core particle; and
    b. timed pulsatile release (TPR) beads, wherein said TPR beads comprise:
        i. a nizatidine-containing core particle;
        ii. a pulse coating surrounding said core, said pulse coating comprising ethylcellulose and an enteric polymer;
    wherein said TPR beads when tested in a USP type II apparatus at 50 rpm using a 2-stage dissolution medium (first 2 hours in 700 ml 0.1 N HCl at 37° C. followed by a dissolution in a pH of 6.8 obtained by the addition of 200 ml of pH modifier) exhibit a dissolution profile substantially corresponding to the following pattern:
after 2 hours, 0–25% of the total nizatidine is released;
after 3 hours, 15–80% of the total nizatidine is released; and
after 4 hours, not less than 60% of the total nizatidine is released.

21. A pharmaceutical dosage form as defined in claim 20, wherein said dissolution profile substantially corresponds to the following pattern:
after 2 hours, 0–15% of the total nizatidine is released;
after 3 hours, 20–65% of the total nizatidine is released; and
after 4 hours, not less than 70% of the total nizatidine is released.

22. A pharmaceutical dosage form as defined in claim 20, wherein the dissolution profile substantially corresponds to the following pattern:
after 2 hours, 0–5% of the total nizatidine is released;
after 3 hours, 30–50% of the total nizatidine is released; and
after 4 hours, not less than 80% of the total nizatidine is released.

23. A pharmaceutical dosage form as defined in claim 20, wherein the core particle is a non-pareil sugar seed coated with nizatidine in a polymeric binder or the core particle is particle prepared by granulation and milling or extrusion/spheronization to form a core particle containing nizatidine.

24. A pharmaceutical dosage form as defined in claim 20, wherein said enteric polymer is selected from the group consisting of esters of cellulose, polyvinyl acetate phthalate, pH-sensitive methacrylic acid-methylmethacrylate copolymers, shellac and derivatives thereof.

25. A pharmaceutical dosage form as defined in claim 24, wherein said enteric polymer is selected from the group consisting of cellulose acetate phthalate, hydroxypropyl methylcellulose phthalate, hydroxypropyl methylcellulose succinate and combinations thereof.

26. A pharmaceutical dosage form as defined in claim 20, wherein said pulse coating further comprises a plasticizer.

27. A pharmaceutical dosage form as defined in claim 26 wherein said plasticizer is selected from the group consisting of triacetin, tributyl citrate, tri-ethyl citrate, acetyl tri-n-butyl citrate, diethyl phthalate, dibutyl sebacate, polyethylene glycol, polypropylene glycol, castor oil and acetylated mono- and di-glycerides and mixtures thereof.

28. A pharmaceutical dosage form as defined in claim 20, wherein said ethylcellulose and said enteric polymer are present in said pulse release coating at a ratio from 4:1 to 1:2.

29. A pharmaceutical dosage form as defined in claim 28, wherein said ratio of ethylcellulose to enteric polymer is from 2:1 to 1:1.

30. A pharmaceutical dosage form as defined in claim 29, wherein said enteric polymer is hydroxypropyl methylcellulose phthalate.

31. A pharmaceutical dosage form as defined in claim 30, wherein said ratio is approximately 1:1.

32. A dosage form as defined in claim 20, wherein said IR beads provide a loading dose by releasing substantially all of the nizatidine contained in said IR beads within the first hour after administration of the dosage form.

33. A pharmaceutical dosage form as defined in claim 20, wherein said IR beads and TPR beads are present in a ratio from about 3:1 to 1:3.

34. A pharmaceutical dosage form as defined in claim 33, wherein said IR beads and TPR beads are present in a ratio from about 2:1 to 1:2.

35. A pharmaceutical dosage form as defined in claim 20, wherein the total weight of the coatings on the TPR beads is 10–60 weight % based on the total weight of the coated particles.

36. A pharmaceutical dosage form as defined in claim 20 said immediate release (IR) beads contain a total of about 75 mg of nizatidine and said timed pulsatile release (TPR) beads contain a total of about 75 mg of nizatidine.

37. A method for the preparation of the dosage form of claim 1, comprising the steps of:
a. preparing a nizatidine-containing core to form IR beads;
b. coating the IR bead with a mixture of plasticized ethylcellulose and an enteric polymer to form a TPR bead; and
c. filling capsules with IR beads and TPR beads at a ratio from 3:1 to 1:3.

38. The method of claim 37, wherein said nizatidine-containing core is produced by coating a particle selected from the group consisting of non-pareil seeds, acidic buffer crystals and alkaline buffer crystals with a water soluble film-forming composition comprising nizatidine and a polymeric binder.

39. The method of claim 37, wherein said nizatidine-containing core is produced by granulating and milling and/or by extrusion and spheronization of a polymer composition containing nizatidine.

40. A method of providing a patient with a timed, sustained release of nizatidine which comprises administering to said patient a dosage form of claim 20.

41. The method according to claim 40, wherein said dosage form is administered orally.

42. The method according to claim 40, wherein said dosage form is administered two times a day.

43. The method according to claim 42, wherein said dosage form is administered at night and in the morning.

44. A method of providing a patient with timed, sustained release of nizatidine which comprises administering to said patient a dosage form of claim 36 two times a day.

45. A method of providing a patient with a timed sustained release of nizatidine which comprises administering to said patient a sufficient amount of a dosage form of claim 36 to provide a total of 300 mg of nizatidine once a day.

46. The method of claim 45 wherein said dose is administered in the evening.

* * * * *